US007930924B2

(12) United States Patent
Krogh et al.

(10) Patent No.: US 7,930,924 B2
(45) Date of Patent: Apr. 26, 2011

(54) SYSTEM FOR THE ONLINE MEASUREMENT OF VOLATILE AND SEMI-VOLATILE COMPOUNDS AND USE THEREOF

(75) Inventors: Erik Thomas Krogh, Nanaimo (CA); Christopher G. Gill, Nanaimo (CA)

(73) Assignee: Vancouver Island University, Nanaimo, BC (CA)

( * ) Notice: Subject to any disclaimer, the term of this patent is extended or adjusted under 35 U.S.C. 154(b) by 615 days.

(21) Appl. No.: 11/864,572

(22) Filed: Sep. 28, 2007

(65) Prior Publication Data

US 2009/0084157 A1 Apr. 2, 2009

(51) Int. Cl.
*G01N 30/02* (2006.01)
(52) U.S. Cl. .......................................................... 73/23.4
(58) Field of Classification Search .................. 73/23.4, 73/23.35
See application file for complete search history.

(56) References Cited

U.S. PATENT DOCUMENTS

| 3,926,561 | A | * | 12/1975 | Lucero | 436/178 |
| 3,997,297 | A | * | 12/1976 | Jenkins et al. | 436/153 |
| 4,116,042 | A | * | 9/1978 | Jenkins et al. | 73/23.39 |
| 5,492,838 | A | * | 2/1996 | Pawliszyn | 436/178 |
| 5,766,954 | A | * | 6/1998 | Freedman et al. | 436/144 |
| 6,477,905 | B1 | * | 11/2002 | Mitra | 73/863.12 |
| 7,509,837 | B2 | * | 3/2009 | Lubkowitz et al. | 73/23.35 |

OTHER PUBLICATIONS

Thammakhet et al, Microtrap modulated flame ionization detector for on-line monitoring of methane, Journal of Chromatography A, Mar. 10, 2005, 243-248, 1072, Elsevier.
Jonsson & Mathiasson, Membrane-based techniques for sample enrichment, Journal of Chromatography A, 2000, 205-225, 902, Elsevier.
Yang et al, Membrane Extraction with a Sorbent Interface for Capillary Gas Chromatography, Analytical Chemistry, Apr. 15, 1994, 1339-1346, vol. 66, No. 8.
Kostiainen.R, Purge and Membrane with ECD. A New Screening Method for Chlorinated Aliphatic Hydrocarbons. Chromatographia, Jul. 1995, 0034-03, vol. 41, No. 1/2.

\* cited by examiner

*Primary Examiner* — Daniel S Larkin
(74) *Attorney, Agent, or Firm* — Klarquist Sparkman, LLP (57) ABSTRACT

A system and method of measuring volatile and semi-volatile reduced organic compound content and volatile and semi-volatile oxidized organic compound content in a sample, using a dual detection system is provided. The method comprises introducing the sample into a semi-permeable membrane introduction interface, sweeping permeate from the membrane introduction interface with a sweep gas, splitting the permeate into a first stream and a second stream, essentially simultaneously detecting volatile and semi-volatile reduced organic compounds and oxidized and semi-volatile organic compounds with a flame ionization detector and an electron capture detector, and computing differences in detector signals, thereby measuring volatile and semi-volatile reduced organic content and volatile and semi-volatile oxidized organic compound content in the sample.

29 Claims, 5 Drawing Sheets

SYSTEM FOR THE ONLINE MEASUREMENT OF VOLATILE AND SEMI-VOLATILE COMPOUNDS AND USE THEREOF

FIELD

The present technology is a system and method of measuring, in real-time, volatile and semi-volatile molecules in a sample, using a multiple detection system. More specifically, the system is a portable system comprising a semi-permeable membrane interface in gaseous communication with a flame ionization detector and an electron capture detector, in parallel.

BACKGROUND

A growing number of analytical applications such as rapid screening of environmental samples, first response incident monitors and industrial scale process monitoring/control require sensitive real-time techniques which are accessible, rugged and relatively inexpensive.

It is well-documented that many byproducts of chlorine-mediated disinfection are putative or confirmed toxins and carcinogens; therefore, it is important to be able to monitor for their presence in drinking waters both during and after disinfection. Furthermore, the widespread use and storage of hydrocarbon fuels has resulted in numerous environmental releases into both ground and surface waters. Of particular concern, is the introduction of hydrocarbons into the environment via storm water run-off and leaking storage tanks. Rapid screening of a large number of samples will greatly facilitate the location of contaminated sites and point sources.

Currently, the accepted method for the analysis of volatile organic compounds (VOCs) and volatile disinfection byproducts (DBPs) in aqueous samples is purge-and-trap gas chromatography/mass spectrometry (P&T-GC/MS). This reliable analytical strategy requires a time-consuming chromatographic separation step, increasing the duty cycle analysis time (trap plus separation) and effectively reducing its utility as a real-time monitoring platform. As an alternative analytical technique, membrane introduction mass spectrometry (MIMS) was developed as a direct, real-time method for the analysis of volatile and semi-volatile organic compounds (VOC/SVOCs). Many drinking water disinfection byproducts (e.g. chloroform, dichloroacetonitrile) fall within this group and are easily and efficiently measured by MIMS. In this approach, sample is flowed over a semi-permeable membrane that provides on-line pre-concentration and permeation of analytes while excluding the bulk sample matrix. Analyte(s) are subsequently transferred (often by a carrier gas) to a mass spectrometer for detection. The online characteristics of MIMS (e.g. no sample preparation or chromatographic separation steps) make it ideal for the direct, real-time monitoring of analytes in complex samples. However, because mass spectrometry requires a vacuum system and relatively delicate components, it is inherently more fragile, therefore, is not amenable for widespread use in portable instrumentation. Additionally, the use of mass spectrometers requires a relatively high degree of technical proficiency in most cases, and although the cost of MS has dropped considerably in the past few years, it is generally considered too expensive for widespread use in municipal drinking water treatment facilities (e.g. online DBP monitoring) or storm water collection systems (e.g. VOC/SVOC contamination testing).

A number of membrane based techniques have been developed for direct analysis of samples and are reviewed recently by Jonsson and Mathiasson (J. Chromatogr. A, 902 (2000) p. 205-225). For example, membrane extraction with a sorbent interface (MESI) uses a hollow fiber membrane that is immersed in an aqueous sample. Volatile analytes permeate through the membrane and are stripped from the other side by a carrier gas, which is then flowed into a sorbent trap where analytes are integrated for thermal desorption onto a GC column. Detection is generally performed with a flame ionization detector (FID). Although MESI is a sensitive and selective methodology that can be programmed to provide chromatograms at regular, frequent intervals, it does not allow for continuous monitoring in real-time.

Thammakhet et. al. (J. Chromatogr. A, 1072(2) (2005) p. 243-248) employed an automated system with an adsorbent microtrap and thermal desorption inline with an FID to measure methane in gas samples, providing rapid data acquisition with no sample preparation. Purge-and-membrane with an electron capture detector (ECD), a similar technique, also avoids chromatographic separation. Instead, helium is bubbled through an aqueous sample, purging volatile and semivolatile analytes, which are subsequently collected by a hollow fiber membrane, followed by thermal desorption and detection. Although analytical quantification with purge-and-membrane ECD has been shown to be successful, it requires the complete purging of analytes from a sample of known volume, making it less suited for continuous duty real-time monitoring scenarios.

It is an object of the present technology to overcome the deficiencies of the prior art.

SUMMARY

In one embodiment of the technology, a method of measuring volatile and semi-volatile reduced organic compound content and volatile and semi-volatile oxidized organic compound content in a sample, using a dual detection system is provided. The method comprises:
introducing the sample into a membrane introduction interface to obtain a permeate;
sweeping the permeate from the membrane introduction interface with a sweep gas; splitting the permeate into a first stream and a second stream;
essentially simultaneously detecting the volatile and semi-volatile reduced organic compounds in the first stream with a suitably selected first detector and the volatile and semi-volatile oxidized organic compounds in the second stream with a suitably selected detector; and
computing differences in detector signals from the first and the second detectors, thereby measuring aggregate volatile and semi-volatile reduced organic content and volatile and semi-volatile,oxidized organic compound content in the sample.

In one aspect of the method, the oxidized organic compounds are volatile organic halides.

In another aspect the method further comprises detecting the volatile reduced organic compounds with a flame ionization detector and detecting the volatile organic halides with an electron capture detector.

In another aspect of the method, the flame ionization detector is a flameless ionization detector.

In another aspect the method comprises conducting the method in real-time.

In another aspect of the method, sweeping is effected with helium as the sweep gas.

In another aspect of the method, sweeping is effected with ambient air as the sweep gas.

In another aspect of the method, the organic halides are selected from the group consisting of carbon tetrachloride, dichloroacetonitrile, chloroform, iodobenzene and 1,1,2-trichlorotrifluroethane.

In another aspect of the method, the organic halide is chloroform.

In another aspect of the method, the membrane introduction interface is a thermally assisted membrane introduction interface.

In another embodiment of the technology, a method of measuring volatile and semi-volatile reduced organic compound content and volatile and semi-volatile oxidized organic compound content in a sample, using a multiple detection system is provided. The method comprises:
introducing the sample into a membrane introduction interface to obtain permeate;
sweeping the permeate from the membrane introduction interface with a sweep gas;
splitting the permeate into at least two streams;
essentially simultaneously detecting the reduced organic compounds in a first stream with a suitably selected first detector, the oxidized organic compounds in a second stream with a suitably selected second detector and other classes of volatile and semi-volatile compounds in additional streams with detectors suitable for detecting said other classes of volatile and semi-volatile compounds; and
computing differences in detector signals, thereby measuring aggregate volatile and semi-volatile reduced organic content and volatile and semi-volatile oxidized organic compound content in the sample.

In one aspect of the method, the sweeping is effected with ambient air as the sweep gas.

In another aspect of the method, the organic halides are selected from the group consisting of carbon tetrachloride, dichloroacetonitrile, chloroform, iodobenzene and 1,1,2-trichlorotrifluroethane.

In another aspect of the method, the organic halide is chloroform.

In another embodiment of the technology, a method of measuring, in real-time, volatile organic halide content and volatile organic compound content in a sample, using a dual detection system is provided. The method comprises:
introducing the sample into a membrane introduction interface to obtain permeate;
sweeping the permeate from the membrane introduction interface with a sweep gas;
splitting the permeate into a first stream and a second stream;
essentially simultaneously detecting the volatile organic compounds in the first stream with a flameless flame ionization detector and the volatile organic halides in the second stream with an electron capture detector; and
computing differences in detector signals from the flameless flame ionization detector and the electron capture detector, thereby measuring, in real-time volatile organic halide content and volatile organic compound content in the sample.

In one aspect of the method, sweeping is effected with ambient air as the sweep gas.

In another aspect of the method, the organic halides are selected from the group consisting of carbon tetrachloride, dichloroacetonitrile, chloroform, iodobenzene and 1,1,2-trichlorotrifluroethane.

In another aspect of the method, the organic halide is chloroform.

In another embodiment of the technology, a portable system to measure volatile and semi-volatile organic halide content and volatile and semi-volatile organic compound content in a sample is provided. The system comprises:
a suitably selected membrane introduction interface; and
a flame ionization detector and an electron capture detector in gaseous communication with the interface and in parallel to one another.

In one aspect of the technology, the membrane introduction interface is a thermally assisted membrane interface.

In one aspect the portable system further comprises a hydrogen source.

In another aspect of the portable system, the flame ionization detector is a flameless flame ionization detector.

In another aspect the portable system further comprises of at least one additional selected detector in suitable gaseous communication with the interface.

In another aspect of the portable system, the at least one additional detector is arranged in parallel to the first and the second detectors.

In another aspect of the portable system, the at least one additional detector is arranged in series to one of the first and the second detectors.

In another aspect the portable system further comprises a carrying case.

The foregoing and other objects, features, and advantages of the invention will become more apparent from the following detailed description, which proceeds with reference to the accompanying figures.

DETAILED DESCRIPTION

The following term definitions are provided solely for the benefit of the reader, and should not be construed to limit the terms to any specific examples provided, or to be definitions which would be narrower than accepted by persons of ordinary skill in the art.

A semi-permeable membrane is a device that pre-concentrates certain molecular species and allows for the passage of certain molecular species from one side to the other, while blocking the passage of other molecular species, such as the bulk sample matrix. Semi-permeable membranes include, but are not limited to, polymer membranes, micro-porous membranes, and supported liquid membranes A membrane interface is a device that makes direct contact between two different media, such as the sample and a sweep gas that transports analytes to a detection system. Membrane interfaces can be constructed in a variety of configurations including but not limited to flat sheet membranes, capillary hollow fiber membranes, and thermally assisted membrane interfaces, in which the membrane is heated to establish a temperature gradient opposing the analyte concentration gradient.

A number of detectors are suitable for measuring VOC, SVOC, and VOX, either alone or when in combination with other detectors. One skilled in the art would be able to select the suitable detectors and arrange them in a suitable configuration to provide the desired results.

A destructive detector is one that destroys the sample. Destructive detectors may be either the terminal detector in a system of detectors in series, or may be in a parallel system. Examples of destructive detectors are:

1. Portable mass spectrometers (MS), which detect all volatile and semivolatile organic compounds (VOC/SVOCs) providing selectivity based upon the masses of the molecules.
2. Residual Gas Analyzers (RGA), mass spectrometers that detect smaller mass volatile molecules with the same selectivity as that of the MS.
3. Flame Photometric Detectors (FPD), which are selective detectors based upon optical emissions from a flame. They can be used to selectively give signals for VOC/SVOCs containing sulfur, phosphorus, halogens, nitrogen as well as selected metals such as tin, chromium, selenium and germanium, depending upon the optical filter used. As an example application, sulfur species such as thiols and sulfides found commonly in pulp mill effluent would be readily detected by a MI-FPD system. In addition, nitrogen containing molecules such as commonly found in explosive compositions would also be suitable for detection by a MI-FPD system.
4. Atomic Emission Detectors (AED), which are based upon detecting a wide range of VOC/SVOCs based upon optical emissions created in a microwave plasma in helium. A wide range of atomic signals can be monitored, including nitrogen, phosphorus, sulfur, carbon, silicon, mercury, bromine, chlorine, hydrogen, deuterium and fluorine. This is a polyfunctional detector (like MS), capable of simultaneously detecting multiple types of molecules. An example application for a MI-AED would be the detection of phosphate and phosphonate species, such as chemical warfare agents and organo-pesticides. In addition, the analyte species and examples listed for detector 3 (above) would also be suitable for detection by MI-AED.
5. Sulfur Chemiluminescence Detectors (SCD), which are based upon the chemiluminescent reaction between certain VOC/SVOC molecules containing sulfur and ozone. An MI-SCD is suitable for detection of VOC/SVOC resin hardening catalysts from industrial plastic forming activities as well as thiols and sulfides found in industrial or other emissions.
6. Thermionic Detectors (TID), which are based upon a flame detector with a heated rubidium silicate bead. A TID selectively detects sulfur and phosphorus containing VOC/SVOCs. Sample applications for MI-TID include detection of phosphate and phosphonate species, such as chemical warfare agents and organo-pesticides, as well as thiols and sulfides found in industrial or other emissions.
7. Photoionization Detectors (PID), which are based upon vacuum ultra-violet photoionization of most VOC/SVOC molecules. This detector is most sensitive for aromatic hydrocarbons, organosulfur and organophosphorus compounds that are easily photoionized. This would include a wide range of VOC/SVOC pesticides as well as chemical warfare agents. In addition hydrocarbon contamination would also be readily monitored by MI-PID, as aromatic molecules such as the BTEX suite (benzene. toluene, ethylbenzene and xylene) are commonly found in hydrocarbon mixtures. A PID can also detect sulfur-containing compounds, such as thiols and sulfides found in industrial or other emissions.
8. Electrolytic Conductivity Detectors, which are available in both "wet" (e.g. hall type) and dry configurations. These detectors selectively detect halogen, nitrogen or sulfur containing VOC/SVOCs, depending upon the reaction gas used in a heated nickel reactor, and/or the solvent used in the conductivity detection cell. The dry type detector is only responsive to bromine and chlorine containing VOC/SVOCs. Therefore this detection strategy would be suitable for explosive residues (molecules containing nitrogen), thiols and sulfides (containing sulfur) and halogenated disinfection byproducts in water (e.g. chloroform, trichloroethylene).
9. Flame ionization detectors (FID), which detect the ions generated by the combustion of carbon containing molecules in a hydrogen/air flame, and are "universal" in that they provide a signal for all VOC/SVOC molecules containing at least one carbon atom. They are particularly excellent for the detection of hydrocarbon molecules.
10. Flameless ionization detector (FLID), which is a modified form of an FID that uses a hot filament instead of a hydrogen flame to combust analytes. They are less sensitive than FID detectors, but are much simpler to operate. FLID detectors are suitable for the same analytes as FID detectors.

A non-destructive detector is one that does not destroy the sample. Non-destructive detectors can be located anywhere in a system of detector in series or can be in parallel. Examples of non-destructive detectors include:

1. Thermal Conductivity Detectors (TCD), which detect all VOC/SVOCs based upon differential thermal conductivity of the carrier gas. Generally they are classified as "universal detectors," giving a signal for any molecule other than the carrier gas. The MI-TCD can detect all VOC/SVOCs, but can also detect molecules not possible with FID (e.g. carbon dioxide, nitrogen, xenon etc.), as the analyte is not required to be combustible for detection. The MI-TCD is suitable for monitoring of carbon dioxide from industrial waste destruction in a treatment facility.
2. Fourier Transform Infra-Red Detector (FTIR-D), which use an infrared absorbance spectrophotometer to provide infra-red spectroscopic molecular signatures for VOC/SVOC molecules. The FTIR-D provides both a signal and a confirmatory identity (at least functional group identity) for unknown molecules. An MI-FTIR-D system would have a broad range of applications in detecting VOC/SVOCs and provides more detail about the detected molecules. A sample application would include the monitoring of synthetic musk fragrance molecules from personal care products in wastewaters.

3. Electron capture detector (ECD), which is sensitive to analytes with a high electron affinity based on their ability to disrupt a stream of beta particles. This includes halogenated molecules and nitro species, making, as examples, the MI-ECD a suitable for the detection of nitrogen containing explosive molecules and halogen containing drinking water disinfection byproducts.

On-line measurements provide an analytical signal by passing the sample through a device without the need for subsequent sample handling. On-line measurements include real-time measurements.

Real-time measurements provide analytical signals from a device while the sample is being introduced in a continuous mode of operation. All real-time measurements are on-line, whereas not all on-line measurements provide real-time data.

Analyte refers to a particular molecule or group of molecular species of interest.

Permeate refers to a sample (analyte) after passage through a membrane introduction interface.

Analytes and permeates include VOC, SVOC, and VOX. The following is a non-exhaustive list: aromatics, including, without limitation, benzo-fluoranthene, benzyl alcohol, benzene, toluene, ethyl benzene; biphenyls, including, without limitation, polychlorinated biphenyls, polybrominated biphenyls, tetrabromo-diphenylether, pentabromo-diphenylether; chlorofluorocarbons, including, without limitation, di-chloro di-fluoroethane, tri-chloro-fluoroethane, bromochloro di-fluoromethane, freons; cycloalkyl halides, including, without limitation, dichlorocyclopropane, chlorocyclohexane, 2-chloro-1-isopropylcyclopropane; disinfection by-products, including, without limitation, chloroform, trihalomethane, dichloromethane, dichloroacetonitrile, cyanogenchloride; halogenated alkenes, including, without limitation, trans-1,2-dichloroethene, 2-methyl-3-chloropropene, trichloroethylene, 1-trifluoromethyl-3-chlorobenzene, 1,3-dibromo-3-chloropropane; halogenated esters, including, without limitation, methyl 3-chloro-4-methoxybenzoate, 2,4-dichlorobutyl ethanoate; hydrochlorofluoro compounds, including, without limitation, dichlorofluorethane, pentafluorodichloropropane, 1,1-dichloro-1-fluoroethane, 2-chloro-1,1,1,2-tetrafluoroethane; phenols, including, without limitation, 4-Chloro-3-methylphenol, 2-chlorophenol, 2,6-dichlorophenol, pentachlorophenol, 2,3,4,6-tetrachlorophenol, 2,4,5-trichlorophenol, 2,4,6-trichlorophenol; polyhalogenated alkanes, including, without limitation, 1,1,2-trichlorotrifluoroethane, 1,2-dichlorohexafluorocyclobutane, 1,1-dichloroethane, 1,1,2-trichloroethane, 1,1,1-trichloroethane; and polyhalogenated alkenes, including, without limitation, trichloroethylene, hexachlorobutadiene, hexachlorocyclopentadiene, tetrachloroethylene; polyhalogenated alkynes, including, without limitation, dichloroethyne.

Volatile compounds (VOC) are molecules characterized by a relatively high vapor pressure, typically greater than about 1,000 Pa.

Semi-volatile compounds (SVOC) are molecules with vapor pressures in the range of from about 0.1 Pa to about 1,000 Pa.

Volatile and semi-volatile organic compounds with one or more halogen, nitrogen, oxygen, sulfur, phosphorus or other element attached as (part of) an oxidized functional group are referred to as oxidized organic compounds (VOX).

A membrane introduction interface with dual FID/ECD (MIFID/ECD) system is a portable system capable of measuring, in real-time, volatile and semi-volatile molecules in a sample, using a multiple detection system that can provide two signals. The relative intensities of the FID and ECD channels are used to distinguish between reduced organic compounds (VOC) (for example, hydrocarbons) and oxidized organic compounds (VOX) (for example, halocarbons). Useful aggregate information regarding VOC/VOX concentration levels can be obtained, providing a direct indication of contaminant load. The dual MIFID/ECD system can allow real-time monitoring of these compounds at parts-per-trillion levels, without sample manipulation. The simplicity and lack of vacuum requirements makes the dual MIFID/ECD system amenable for remote use and multiple deployments in process control scenarios. This rugged system provides an alternative to MIMS while still maintaining high sensitivity. Further, the system allows for a short analytical duty cycle of less than about 30 seconds and continuous monitoring, providing direct measurements for different compound classes in a real-time, on-line fashion.

EXAMPLE 1

Figure 1:
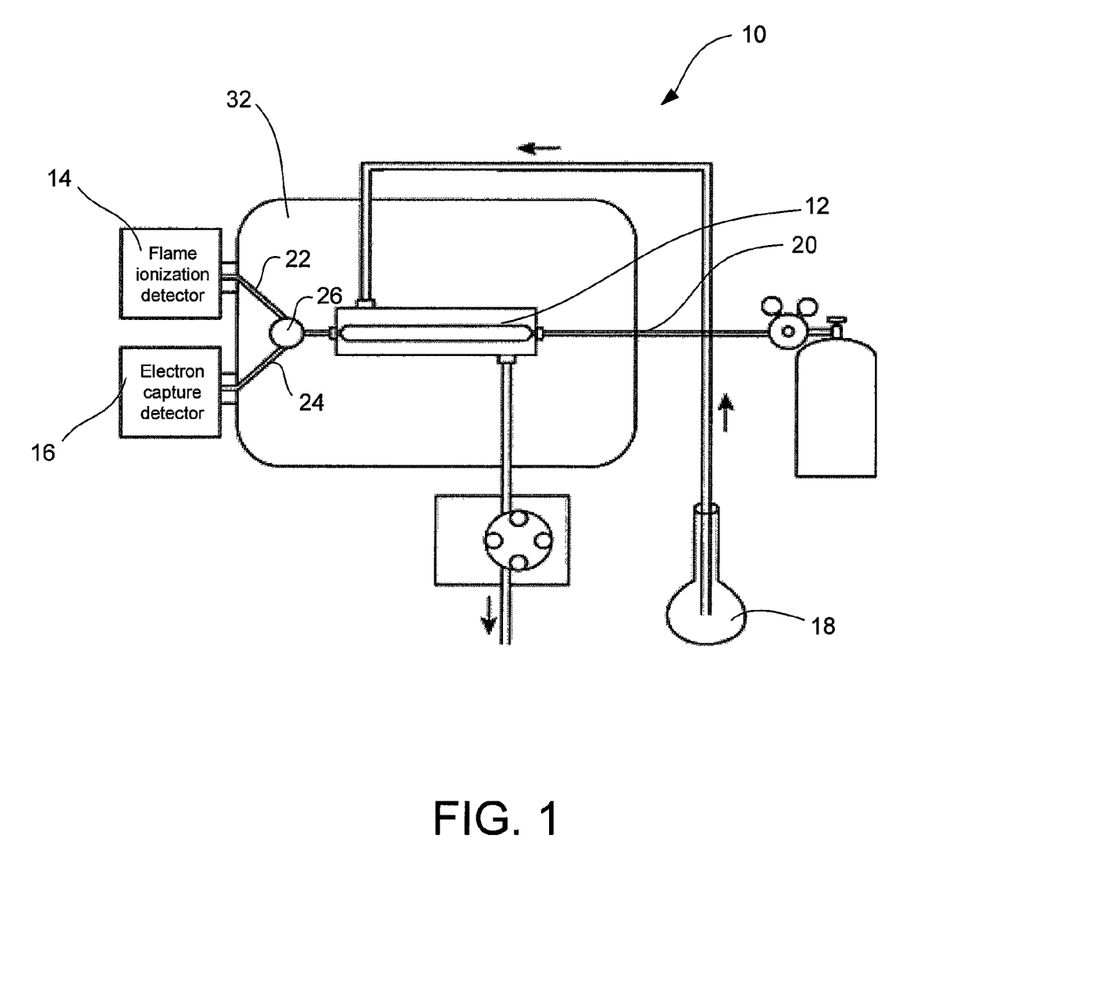
FIG. 1 is a schematic representation of the dual MIFID/ECD system in accordance with an embodiment of the present technology

FIG. 1 illustrates one embodiment of MIFID/ECD system 10. Online membrane introduction interface 12 is coupled with parallel flame ionization 14 and electron capture 16 detectors. On passing through membrane interface 12, analytes 18 are carried in a helium sweep gas 20 and split into two parallel flows 22 and 24 for simultaneous detection by flame ionization detector 14 and electron capture detector 16. FID 14 is sensitive to reduced hydrocarbon compounds that are efficiently combusted in a hydrogen-air flame. ECD 16 is sensitive to analytes 18 with a high electron affinity based on their ability to disrupt a stream of beta particles. Two signals are obtained, and the relative intensities of FID 14 and ECD 16 channels are used to distinguish between reduced organic carbon compounds (e.g., hydrocarbons) and oxidized organic compounds (e.g., halocarbons).

EXAMPLE 2

Figure 2:
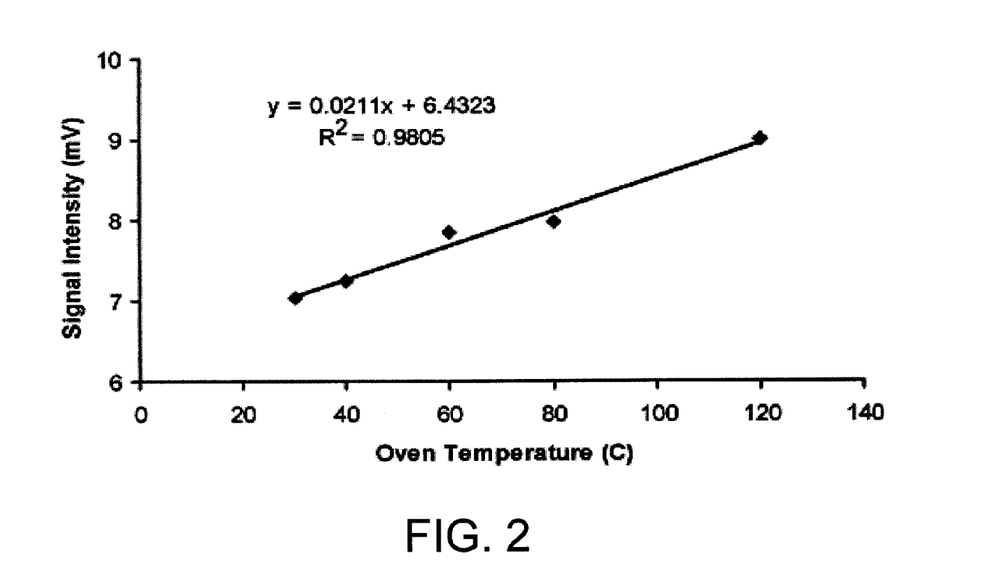
FIG. 2 is a graph showing effect of membrane oven temperature on FID signal intensity from the system of FIG. 1. All measurements made for 140 ppb toluene in an unsplit (MI-FID) system.

The performance of MIFID system 10 was optimized for signal intensity by adjusting sample flow rate, helium sweep gas flow rate, and membrane 12 temperature. Signal intensity was found to increase with sample flow due to increasing analyte 18 loading on membrane 12 and subsequent steady-state flux. Although optimum signal intensity was observed at higher sample flows (greater than about 150 mL/min), a flow rate of 85 mL/min was used in subsequent measurements to minimize sample consumption. Helium sweep gas flow rates were varied from 5 to 25 mL/min and were observed to have a significant effect upon signal intensity, with a maximum signal achieved at a helium flow of 15 mL/min (used in all subsequent, unsplit MIFID measurements). This optimum is likely due to the compensating effects of an increased efficiency of analyte stripping at higher sweep gas flow rates versus analyte dilution and/or deterioration of the FID detector performance at higher flows. FIG. 2 illustrates the effect of membrane oven 32 temperature on signal intensity, with higher temperatures giving rise to stronger signal. This has been determined previously in MIMS applications to be a result of increased analyte permeability and volatility.

EXAMPLE 3

Figure 3:
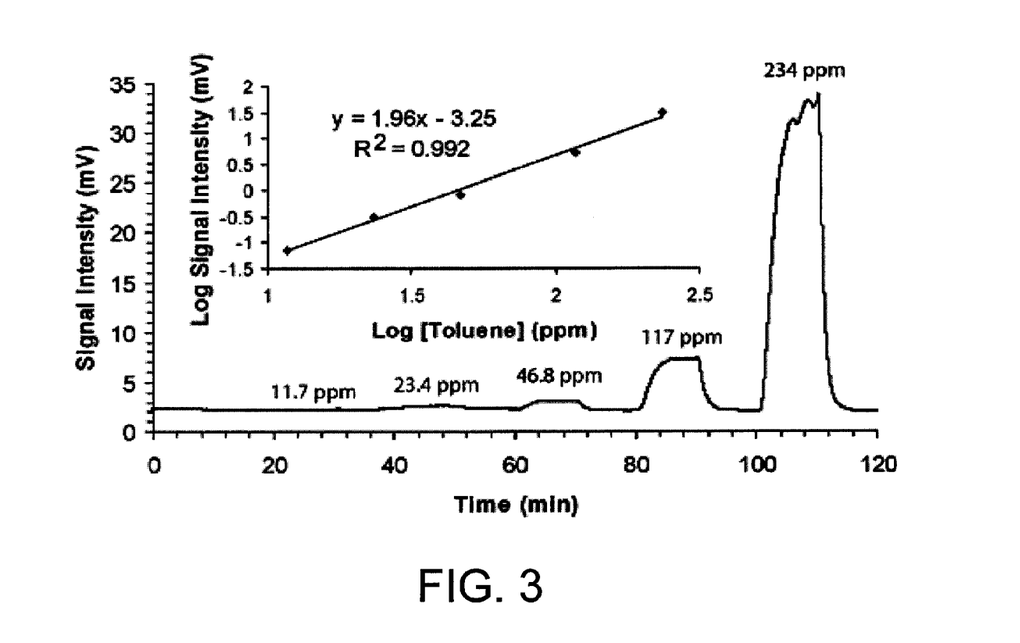
FIG. 3 is a graph showing toluene standards and calibration curve (inset) using membrane introduction flameless ionization detection (MIFLID) in accordance with an embodiment of the present technology.

To develop a simplified system (and to increase potential portability), further experiments were conducted using MIFID system 10 without the continuous flame normally used in FID detectors 14. In these flameless ionization detector (FLID) experiments, hydrogen gas was not used; instead, the FID igniter was placed directly in front of the FID jet. The voltage of the igniter was then increased until it glowed red and was hot enough to ignite and ionize effluent organics carried in the helium flow. Although sensitivity using FLID was significantly lower than that achieved using FID (e.g. ppm compared to pptr for aqueous toluene), there was excellent correlation ($R^2$=0.992) between signal and analyte concentration in a log/log calibration curve, as seen in FIG. 3. An experiment was also conducted where ambient air (17 mL/min) was used as a sweep gas (instead of helium) using a second head on the peristaltic sample pump. As seen in FIG. 3, this configuration also gave ppm sensitivity for toluene in water and eliminated the requirement for compressed gas cylinders. Because MIFLID using ambient air as the sweep gas requires only a power source, this instrument could readily be adapted as a portable, inexpensive monitor for bulk, volatile hydrocarbons.

Referring again to FIG. 1, membrane interface 12 was connected to both ECD 16 and FID 14 detectors via Y-connector 26 to facilitate simultaneous detection and quantification of multiple species. MIFID/ECD system 10 was employed to determine the detection limits and relative response factors for a variety of compounds in water. The table below shows response factors relative to toluene and detection limits for MIFID and MIECD. ECD detection showed a range of detection limits: from 200 pptr for methyl iodide to 17 ppm for toluene, whereas the FID showed detection limits ranging from 400 pptr for toluene to 118 ppb for 1,1,2-trichlorotrifluoroethane.

| Compound | Response Factor | | Detection Limit (ppb)[a] | |
|---|---|---|---|---|
| | MIFID | MIECD | MIFID | MIECD |
| Hydrocarbons | | | | |
| Toluene | 1 | 1 | 0.4 | 17000 |
| Benzene | 0.84 | — | 0.4 | — |
| Hexanes | 0.53 | ND[c] | 0.7 | ND |
| Cyclohexane | 0.19 | — | 2.0 | — |
| Gasoline | 0.13 | — | 3.1 | — |
| Halogenated | | | | |
| Carbon tetrachloride | 0.01 | 39000 | 54 | 0.4 |
| Dichloroacetonitrile | — | 26000 | — | 0.7 |
| Chloroform | 0.05 | 12000 | 7.0 | 1 |
| Iodobenzene | 0.01 | 5200 | 43 | 3.3 |
| 1,1,2-trichlorotrifluroethane | 0.003 | 1600 | 118 | 10 |
| Miscellaneous | | | | |
| 2,4-dimethyl-3-pentanone | 0.21 | — | 1.8 | — |
| Isopropanol | 0.13 | — | 2.8 | — |
| Butyraldehyde | 0.03 | — | 11 | — |
| Acetophenone | 0.01 | — | 25 | — |

[a] Detection limits are based on S/N = 3
— Analyte not tested with this detector
ND: Analyte not detected at the concentration measured It should be noted that the ECD sensitivity could be further improved by higher temperature operation; a modest temperature (70° C.) was chosen so there would be no oxidation of the radioactive foil within the detector. For either detector, the sensitivity to individual analytes is influenced by the permselectivity of the analyte in the membrane, which is a function of both the partitioning and diffusion coefficients of the analyte in the membrane material. Furthermore, the overall instrument sensitivity is influenced by the detector response to individual analytes. While the ECD responds only to compounds that can accept electrons (e.g., organic halides), the FID responds to any compounds that can be readily combusted (e.g. compounds containing reduced carbon). As such, the dual detection system of the MIFID/ECD system provides complementary information and a degree of selectivity.

Figure 4:
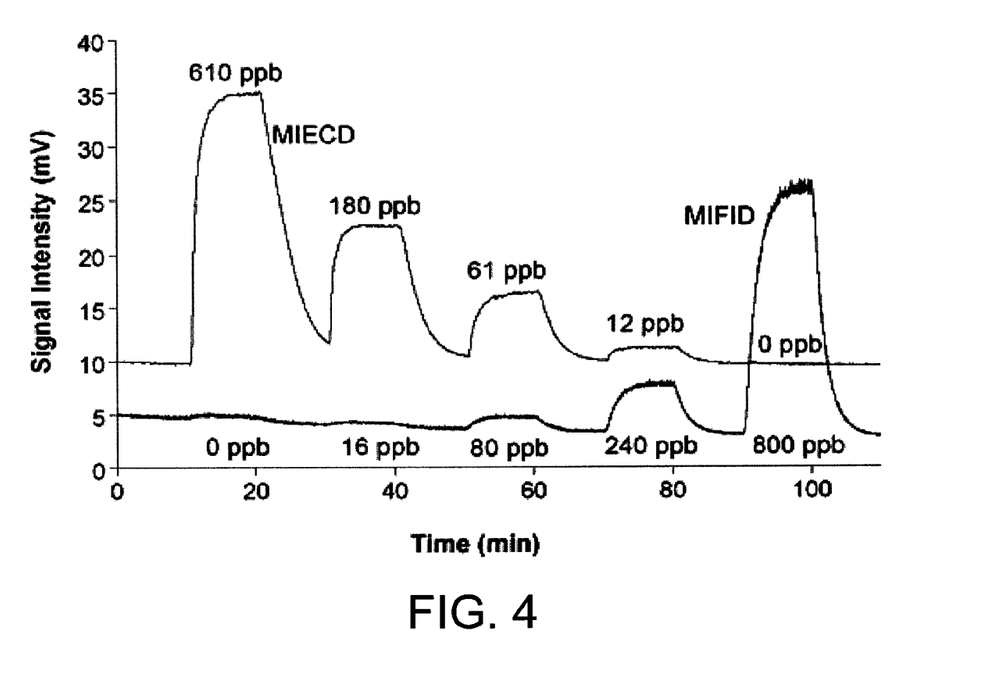
FIG. 4 is a graph showing quantification of carbon tetrachloride and toluene combined standards by the dual MIFID/ECD in accordance with an embodiment of the present technology. Reported concentrations are for carbon tetrachloride (top) and toluene (bottom) present in each combined standard. FID signal was multiplied 75× for comparison purposes.

This selectivity is illustrated in FIG. 4 for a series of measurements using combined aqueous standards containing carbon tetrachloride and toluene with opposing concentrations. Whereas the FID is insensitive to carbon tetrachloride, the ECD is insensitive to toluene. In an experiment in which the chloroform concentration was varied (18.2-445 ppb) in the presence of a constant toluene concentration of 1.2 ppm, (data not shown) the FID signal remained constant, while the ECD signal changed in proportion to the concentration of chloroform. Even with this high hydrocarbon background, the correlation between chloroform concentration and ECD signal intensity was excellent, $y=-2.3x^2+2600x-5300$, $R^2=0.999$ (as a consequence of their narrow linear dynamic range, ECD calibrations more accurately fit with quadratic, rather than linear, functions).

A complementary experiment was carried out in which the toluene concentration was varied (12-600 ppb) with a constant chloroform background concentration of 91 ppb. Again, a very good correlation between toluene concentration and FID signal intensity was obtained ($y=25x-400$, $R^2=0.997$). It should be noted that detecting hydrocarbons in the presence of halogenated organic molecules is prone to some interference because the FID is a more universal detector. This is illustrated by comparing the relative response factors presented in the table above. All of the halogenated compounds tested were detected by the FID, albeit with response factors twenty to a hundred times lower than that for toluene, whereas the response factors for the halogenated compounds on the ECD exceed that of toluene by three or four orders of magnitude. To illustrate this selectivity, in the combined standards results described above and shown in FIG. 4, the concentration of carbon tetrachloride must be only five times the concentration of toluene to give a 5% positive bias for toluene on the FID channel. To achieve the same bias on the ECD, the concentration of toluene must be two thousand times greater than the concentration of carbon tetrachloride.

EXAMPLE 4

The dual MIFID/ECD system was also used to analyze a number of environmental samples and surrogates. In the first application, the dual system was used as a semi-selective sensor for VOCs and VOXs in Vancouver Island drinking water samples. Water samples collected from a variety of municipal water systems and one drilled well were analyzed and are presented in the table below.

| Municipal Water System[†] | Equivalent Concentration[a] (ppb) | |
|---|---|---|
| | Chloroform | Toluene |
| Victoria | 0 | 0 |
| Duncan | 0 | 0 |
| Nanaimo | 78 | 0 |
| Lantzville | 200 | 0 |

-continued

| Municipal Water System[†] | Equivalent Concentration[a] (ppb) | |
|---|---|---|
| | Chloroform | Toluene |
| Parksville | 510 | 0 |
| Chemainus[b] | 0 | 910 |

[†]Single samples collected at municipal tap sources without correlation to chlorine dosing schedules or sampling location within the distribution systems. This data is useful for MIFID/ECD demonstration purposes only and does not necessarily represent the overall distribution system levels.
[a]Concentration reported as the equivalent amount of standard required to generate the observed signal.
[b]Private, drilled well system (industrial use only).

It is important to note that these samples are from single, random collections with no correlation to chlorine dosing schedules or sampling location within the respective distribution systems. As such, these samples represent a demonstration of the MIFID/ECD system and should not be used as an assessment of water quality within these municipalities. Individual analyses were completed in several minutes with no sample preparation or pre-treatment steps. The sample interface was flushed with de-ionized water between samples. As shown in Table 2, three water samples were found to have strong ECD signals, suggesting the presence of halogenated organic compounds. While this ECD data does not allow us to distinguish individual DBPs, it can provide an estimate of the total halogenated DBP concentration. The volatile DBP profile of most drinking waters is dominated by one or two species, such as chloroform or dichloroacetonitrile. As such, the ECD signal can be converted to an equivalent concentration of the predominant DBP (chloroform was used in this case). Different calibrations could be carried out if another VOX species is known to predominate. Because the ECD also responds to hypochlorous acid (present as residual chlorine, see FIG. 5 discussion below), the signal is the sum of the chlorine itself and the disinfection byproducts it produces. If the residual chlorine concentration is known to be significant, its contribution can be subtracted from the total signal.

The FID signal was negligible for the drinking water samples, except for the drilled well water, which had a signal corresponding to an equivalent concentration of 910 ppb toluene. This sample was collected from a well located at the edge of an automotive wrecking yard, which may explain the high levels of hydrocarbon contamination. We simulated this type of contamination by adding 490 ppb of commercial gasoline to a municipal water sample. The resulting signal showed a response factor of 0.13 for gasoline relative to toluene, suggesting that the Chemainus sample could contain ~7 ppm of gasoline. However, due to the high variability of gasoline composition (and concomitant response factors), this number is a crude estimate.

EXAMPLE 5

Figure 5:
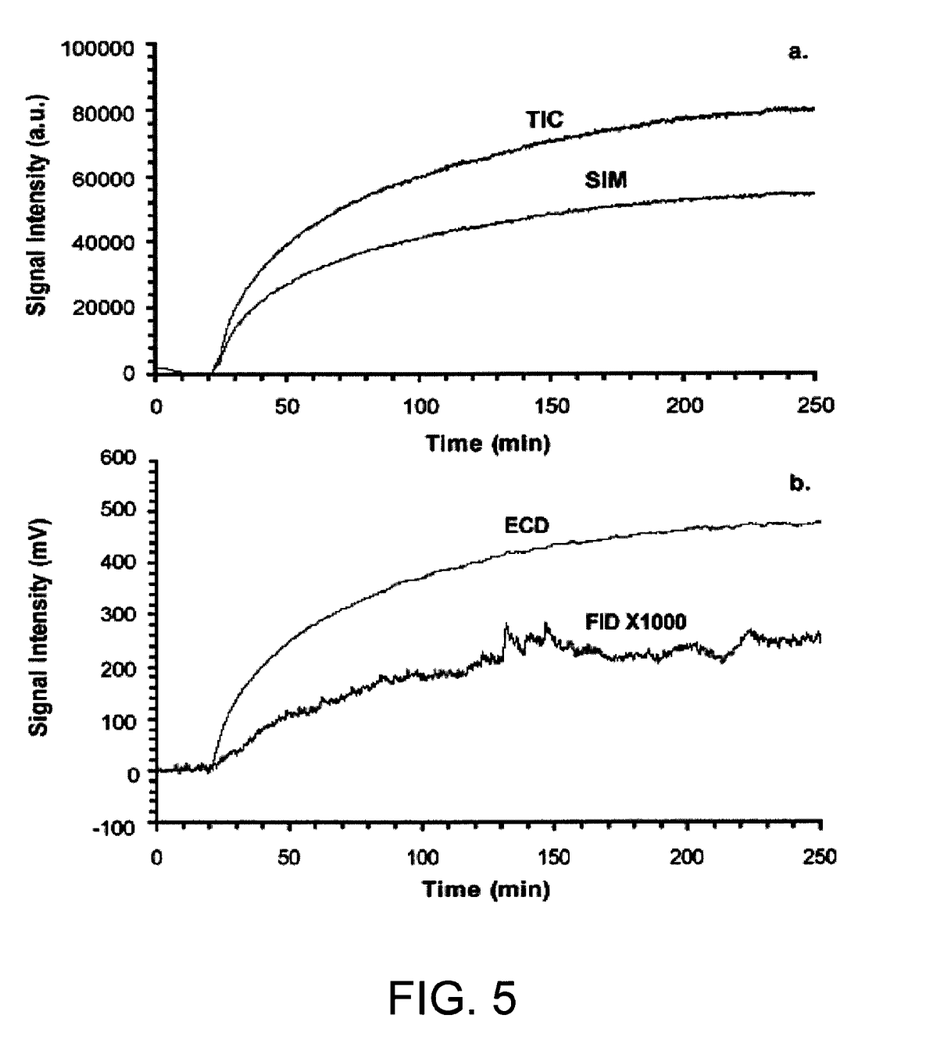
FIG. 5 is a graph showing reaction monitoring for the chlorination of natural surface water as monitored by (a) MIMS and (b) the dual MIFID/ECD system in accordance with an embodiment of the present technology (the FID signal was multiplied 1000× for comparison purposes). Chlorine (equivalent to 10 ppm as C12) was added to sample reservoir at 20 minutes in a re-circulating closed loop.

In addition to its robust and sensitive capabilities for direct analysis in complex matrices, MIFID/ECD can also be used for real-time reaction monitoring. We have employed our system to monitor the real-time formation of disinfection byproducts during natural water chlorination (FIG. 5). For these experiments, active chlorine (equivalent to 10 ppm as $Cl_2$) was added to a natural surface water sample and re-circulated over the membrane interface in a closed loop. Parallel experiments using MIFID/ECD and MIMS were compared. Because chloroform was the dominant volatile disinfection byproduct formed (as verified by MIMS), chloroform standards were used to quantify the signals on each system. FIG. 5 illustrates the results of the MIMS analysis. An equivalent concentration of 221+/−4 ppb chloroform was measured by using the TIC calibration and 213+/−4 ppb using SIM calibration, indicating that chloroform was the dominant volatile DBP formed (~96%). These values agree well with the equivalent chloroform concentration of 212+/−15 ppb determined with the FID signal. However, the ECD signal does not agree as well, over-predicting an equivalent chloroform concentration of 423 ppb. This suggests that the ECD must be responding to species not detected by the other systems, including MIMS.

In a MIMS control experiment where hypochlorous acid was added to re-circulating de-ionized water, no increase over the TIC baseline was seen. However, when the same control was performed on the dual MIFID/ECD system, a substantial increase in signal was seen on the ECD trace but not on the FID trace. This signal is likely due to hypochlorous acid crossing the membrane, which is readily detected by the ECD, but would be undetected by the FID. Further, it would not be detected in the MIMS experiment because its expected fragment ions (m/z 35, 37) are below the full scan low mass cut-off used for this work.

EXAMPLE 6

Figure 6:
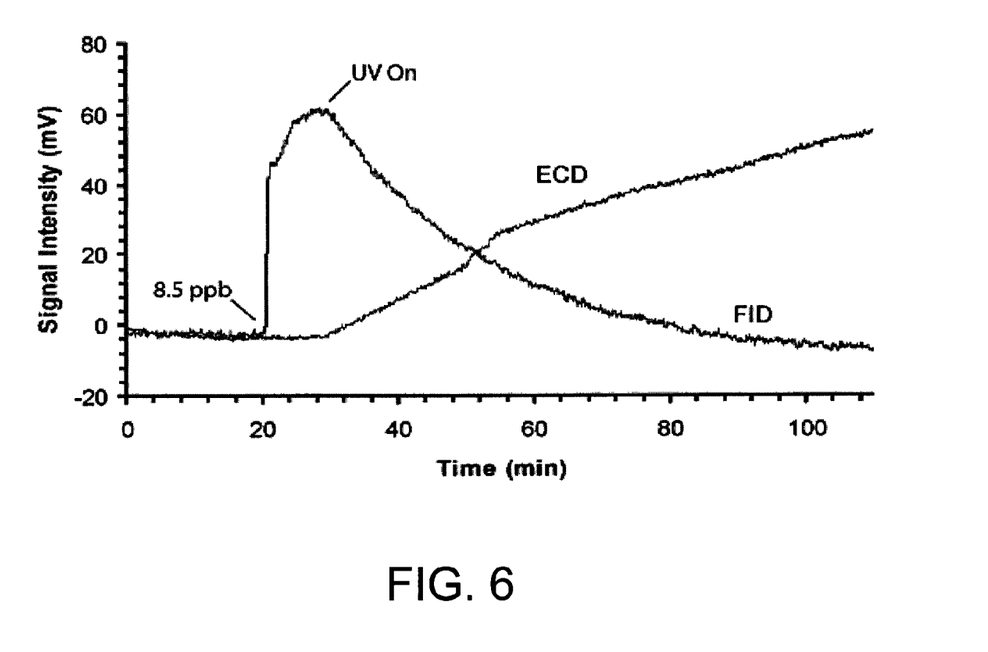
FIG. 6 is a graph showing photo-degradation of toluene in the presence of TiO2/H2O2 monitored using MIFID/ECD of an embodiment of the present technology (the FID signal was multiplied 100× for comparison purposes). Toluene standard was added to de-ionized water in the sample reservoir at 20 minutes (8.5 ppb final concentration) followed by irradiation with 300 nm light at 28 minutes.

The MIFID/ECD for real-time reaction monitoring was also used to follow the degradation of dilute aqueous toluene solutions via a titanium dioxide catalyzed photo-oxidation process, and the results are shown in FIG. 6. In this analysis, aqueous 8.5 ppb toluene and 6.3 mM hydrogen peroxide was re-circulated through a sample reservoir and a photo-reactor. After achieving a steady signal, the UV lamps were turned on and the subsequent loss of toluene was measured by the FID. After an hour, the FID signal dropped to zero, indicating that essentially all the toluene had been degraded, consistent with observations in previous MIMS experiments. The photo-oxidation was simultaneously monitored with the ECD, which showed a steady increase in signal upon turning on the UV lamps. A control was run in which no toluene was added and a similar rise was seen for the ECD signal upon turning on the UV lamps. Because there were no reduced carbon compounds for the hydrogen peroxide to oxidize in this control, the ECD signal likely represents the photolysis of hydrogen peroxide to produce molecular oxygen, which readily crosses the membrane and is detectable by ECD.

EXAMPLE 7

An online membrane introduction interface can be coupled with parallel flame ionization and sulfur chemiluminescence (FID/SCD) to create a system analogous to that shown in FIG. 1. On passing through the membrane, analytes can be carried in a helium sweep gas and split into two parallel flows for simultaneous detection by flame ionization detector (FID) and sulfur chemiluminescence detector (SCD). The FID is sensitive to reduced hydrocarbon compounds that are efficiently combusted in a hydrogen-air flame. The SCD is sensitive to analytes containing sulfur based upon a chemiluminescent reaction with ozone. Two signals can be obtained, and the relative intensities of the FID and SCD channels can be used to distinguish between reduced organic carbon compounds (e.g., hydrocarbons) and sulfur containing organic compounds (e.g. sulfides and thiols).

EXAMPLE 8

An online membrane introduction interface can also be coupled with parallel flame ionization and flame photometric (FID/FPD) detectors, again creating a system analogous to the one seen in FIG. 1. Upon passing through the membrane, analytes carried in a helium sweep gas can be split into two parallel flows for simultaneous detection by flame ionization detector (FID) and flame photometric detector (FPD). The flame photometric detector can be equipped with three different optical filters to select for nitrogen, phosphorous and sulfur. The FID is sensitive to reduced hydrocarbon compounds that are efficiently combusted in a hydrogen-air flame. The FPD can be configured to be sensitive to analytes containing nitrogen, phosphorous and sulfur. Four signals can be obtained, and the relative intensities of the FID and FPD channels can be used to distinguish between reduced organic carbon compounds (e.g., hydrocarbons), compounds containing nitrogen (e.g., nitrogenous explosive residues), compounds containing phosphorus (e.g., chemical warfare nerve gas agents) and compounds containing sulfur (e.g., thiols and sulfides).

EXAMPLE 9

An online membrane introduction interface can also be coupled with an atomic emission detector (AED). Upon passing through the membrane, analytes can be carried in a helium sweep gas for detection by the AED. The AED is sensitive to a range of different compounds based upon the plasma-induced emission of various elements that may be present. Multiple signals could be obtained, and the relative intensities of the various elemental emission channels can be used to distinguish between halogenated compounds (e.g. chlorinated drinking water disinfection byproducts), nitrogen containing organic compounds (e.g., nitrogenous explosive residues), phosphorus containing compounds (e.g., chemical warfare nerve gas agents) and sulfur containing compounds (e.g., thiols and sulfides).

EXAMPLE 10

An online thermally assisted membrane introduction interface can also be coupled with multiple parallel detectors. On passing through the membrane, analytes will be carried in a helium sweep gas and passed through a thermal conductivity detector (TCD) and then split into three parallel streams for simultaneous detection by a flame ionization detector (FID), a thermionic detector (TID) and a flame photometric detector (FPD). The TCD is a non-destructive universal detector which will provide a signal proportional to total mass flux. The FID is sensitive to reduced hydrocarbon compounds that are efficiently combusted in a hydrogen-air flame. The TID selectively detects sulfur (e.g., thiols and sulfides associated with pulp mill and other industrial emissions) and phosphorus containing compounds (e.g., nerve gases and agrochemicals). The FPD can be configured with an optical filter selective for nitrogen containing compounds (e.g., nitrogenous explosive residues). Multiple signals can be obtained, and the relative intensities of each can be used to classify particular VOC/SVOC combinations.

The foregoing is an embodiment of the technology. As would be known to one skilled in the art, variations that do not alter the scope of the technology are contemplated. For example, any semi-permeable membrane sampling interface can be used and two or more complimentary semi-selective detectors can be coupled to the interface, such as any detector employed for gas chromatography. These detectors can provide additional information about the volatile and semi-volatile compounds. For example, these detectors can be used to determine whether VOC/SVOC contain phosphorous (common to many nerve agents) or whether the VOC/SVOC contain nitrogen (common to many explosives).

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of measuring volatile and semi-volatile organic compound content in a sample, using a detection system, said method comprising:
   introducing the sample into a membrane introduction interface to obtain permeate;
   sweeping said permeate from the membrane introduction interface with a sweep gas;
   splitting said permeate into a first stream and a second stream;
   essentially simultaneously detecting said volatile and semi-volatile organic compounds in said first stream with a suitably selected first detector and said volatile and semi-volatile organic compounds in said second stream with a suitably selected second detector, wherein the first detector is a different type than the second detector; and
   computing differences in detector signals from said first and said second detectors, thereby measuring aggregate volatile and semi-volatile organic content in said sample.

2. The method of claim 1 wherein said organic compounds are volatile organic halides.

3. The method of claim 1 comprising detecting said volatile organic compounds with a flame ionization detector and detecting volatile organic halides with an electron capture detector.

4. The method of claim 3 wherein said flame ionization detector is operated in flameless mode.

5. The method of claim 3 where the sweep gas is helium.

6. The method of claim 5 wherein said volatile organic halides are selected from the group consisting of carbon tetrachloride, dichloroacetonitrile, chloroform, iodobenzene and 1,1,2-trichlorotrifluroethane.

7. The method of claim 3 where the sweep gas is ambient air.

8. The method of claim 6 wherein said organic halide is chloroform.

9. The method of claim 1 comprising conducting said method substantially continuously and in real-time.

10. The method of claim 1 wherein said membrane introduction interface is a thermally assisted membrane introduction interface.

11. The method according to claim 1 wherein the detection system comprises dual detectors.

12. The method according to claim 1 wherein the detection system comprises more than two detectors.

13. The method according to claim 1, wherein computing differences in detector signals comprises analyzing relative intensities of detector signal outputs to determine a type or class of compound present in the permeate.

14. The method according to claim 1, wherein computing differences in detector signals comprises analyzing absolute intensities of detector signal outputs to determine a quantity of a compound present in the permeate.

15. The method according to claim 1, wherein the first detector is a flame photometric detector and the method further comprises providing continuous information on volatile and semi-volatile nitro-organic compounds.

16. The method according to claim 1, wherein the sample is a gas sample.

17. The method according to claim 1, wherein the sample is a liquid sample.

18. A method of measuring volatile and semi-volatile organic compound content and volatile in a sample, using a detection system, said method comprising:
   introducing the sample into a membrane introduction interface to obtain permeate;
   sweeping said permeate from the membrane introduction interface with a sweep gas;
   splitting said permeate into at least two streams;
   essentially simultaneously detecting the organic compounds in a first stream with a suitably selected first detector, the organic compounds in a second stream with a suitably selected second detector and other classes of volatile and semi-volatile compounds in additional streams with detectors suitable for detecting said other classes of volatile and semi-volatile compounds, wherein the first detector is a different type than the second detector; and
   computing differences in detector signals thereby measuring aggregate volatile and semi-volatile organic content in said sample.

19. The method of claim 18 wherein said membrane introduction interface is a thermally assisted membrane introduction interface.

20. The method according to claim 18 where the system comprises dual detectors.

21. The method according to claim 18 where the system comprises more than two detectors.

22. The method according to claim 18 where the system comprises at least one additional selected detector in suitable gaseous communication with said membrane introduction interface.

23. The method according to claim 22 wherein said at least one additional detector is arranged in parallel to said flame ionization detector and said electron capture detector.

24. The method according to claim 22 wherein said at least one additional detector is arranged in series to one of said flame ionization detector and said electron capture detector.

25. The method according to claim 18, wherein computing differences in detector signals comprises analyzing relative intensities of detector signal outputs to determine a type or class of compound present in the permeate.

26. The method according to claim 18, wherein computing differences in detector signals comprises analyzing absolute intensities of detector signal outputs to determine a quantity of a compound present in the permeate.

27. The method according to claim 18, wherein the first detector is a flame photometric detector and the method further comprises providing continuous information on volatile and semi-volatile nitro-organic compounds.

28. The method according to claim 18, wherein measuring aggregate volatile and semi-volatile organic content is performed substantially continuously and in real-time.

29. A portable system to measure volatile and semi-volatile organic compound content in a sample, said system comprising:
   a suitably selected membrane introduction interface; and
   a flame ionization detector and an electron capture detector in gaseous communication with said interface and in parallel to one another, wherein the flame ionization detector and the electron capture detector are configured to provide substantially continuous and substantially simultaneous signal outputs.

* * * * *

UNITED STATES PATENT AND TRADEMARK OFFICE
CERTIFICATE OF CORRECTION

| | | |
|---|---|---|
| PATENT NO. | : 7,930,924 B2 | Page 1 of 1 |
| APPLICATION NO. | : 11/864572 | |
| DATED | : April 26, 2011 | |
| INVENTOR(S) | : Krogh et al. | |

It is certified that error appears in the above-identified patent and that said Letters Patent is hereby corrected as shown below:

Column 1, lines 55-56, "fragile, therefore" should read --fragile, and, therefore--.

Column 3, line 4, "trichlorotrifluroethane" should read --trichlorotrifluoroethane--.

Column 3, line 36, "trichlorotrifluroethane" should read --trichlorotrifluoroethane--.

Column 3, line 61, "trichlorotrifluroethane" should read --trichlorotrifluoroethane--.

Column 4, line 11, "comprises of" should read --comprises--.

Column 4, line 32, "technology" should read --technology.--.

Column 4, line 54, "Cl2" should read --$Cl_2$--.

Column 4, line 57, "TiO2/H2O2" should read --$TiO_2/H_2O_2$--.

Column 5, line 10, "membranes" should read --membranes.--.

Column 6, line 20, "benzene." should read --benzene,--.

Column 6, line 51, "detector" should read --detectors--.

Column 6, line 59, "xenon etc." should read --xenon, etc.--.

Column 6, line 65, "use" should read --uses--.

Column 7, line 12, "a suitable" should read --suitable--.

Column 9, line 43, "ND⁶" should read --ND--.

Column 9, line 50, "trichlorotrifluroethane" should read --trichlorotrifluoroethane--.

Column 13, line 7, "phosphorous" should read --phosphorus--.

Column 13, line 11, "phosphorous" should read --phosphorus--.

Column 13, line 62, "complimentary" should read --complementary--.

Column 13, line 67, "phosphorous" should read --phosphorus--.

Claim 6, column 14, line 44, "trichlorotrifluroethane" should read --trichlorotrifluoroethane--.

Claim 18, column 15, line 8, "and volatile" should be deleted.

Signed and Sealed this
Eleventh Day of October, 2011

David J. Kappos
*Director of the United States Patent and Trademark Office*